(12) United States Patent
Bouloussa et al.

(10) Patent No.: US 10,238,110 B2
(45) Date of Patent: Mar. 26, 2019

(54) READY-TO-USE STORABLE METHANOLIC SOLUTION OF A BIOCOMPATIBLE AND BIOCIDAL POLYVINYLPYRIDINE POLYMER

(71) Applicants: Houssam Bouloussa, Oakland, CA (US); Othman Bouloussa, Bordeaux (FR)

(72) Inventors: Houssam Bouloussa, Oakland, CA (US); Othman Bouloussa, Bordeaux (FR)

( * ) Notice: Subject to any disclaimer, the term of this patent is extended or adjusted under 35 U.S.C. 154(b) by 0 days.

(21) Appl. No.: 15/825,517

(22) Filed: Nov. 29, 2017

(65) Prior Publication Data

US 2018/0146669 A1    May 31, 2018

Related U.S. Application Data

(60) Provisional application No. 62/427,464, filed on Nov. 29, 2016.

(51) Int. Cl.
| | |
|---|---|
| *A01N 43/40* | (2006.01) |
| *C08F 8/44* | (2006.01) |
| *A01N 55/00* | (2006.01) |
| *A01N 25/02* | (2006.01) |
| *C08F 26/06* | (2006.01) |
| *C08F 8/42* | (2006.01) |

(52) U.S. Cl.
CPC .......... *A01N 43/40* (2013.01); *A01N 25/02* (2013.01); *A01N 55/00* (2013.01); *C08F 8/42* (2013.01); *C08F 8/44* (2013.01); *C08F 26/06* (2013.01)

(58) Field of Classification Search
CPC ........ A01N 43/40; A01N 25/02; A01N 55/00; C08F 8/42; C08F 26/06; C08F 8/44
See application file for complete search history.

(56) References Cited

U.S. PATENT DOCUMENTS

| | | | | |
|---|---|---|---|---|
| 7,151,139 | B2 * | 12/2006 | Tiller | ..................... A01N 43/40 525/165 |
| 2007/0292486 | A1 | 12/2007 | Sen et al. | |
| 2010/0305289 | A1 | 12/2010 | Jiang | |
| 2012/0276040 | A1 | 11/2012 | Chuang | |

* cited by examiner

*Primary Examiner* — Carlos A Azpuru
(74) *Attorney, Agent, or Firm* — Panitch Schwarze Belisario & Nadel LLP

(57) ABSTRACT

An alcoholic solution of a partially quaternarized polyvinylpyridine polymer is provided. The alcoholic solution has biocidal and biocompatibility properties. The alcoholic solution is ready-to-graft in order to confer biocidal properties on various surfaces and to prevent biofilm formation on such surfaces.

11 Claims, 10 Drawing Sheets

READY-TO-USE STORABLE METHANOLIC SOLUTION OF A BIOCOMPATIBLE AND BIOCIDAL POLYVINYLPYRIDINE POLYMER

CROSS-REFERENCE TO RELATED APPLICATIONS

This application claims priority to U.S. Provisional Patent Application No. 62/427,464, filed on Nov. 29, 2016, entitled "Alcoholic Solution of a Partially Quaternarized Polyvinylpyridine," the entire contents of which are incorporated by reference herein.

BACKGROUND OF THE INVENTION

The present invention generally relates to the field of biocides and, in particular, to an alcoholic solution of a partially quaternarized polyvinylpyridine polymer having both biocidal and biocompatibility properties. The present invention is designed to be a ready-to-use solution for reducing biofilm formation on various surfaces by covalently grafting a biocidally active copolymer using a chloromethylcatechol or iodopropyltrimethoxysilane spacer.

Biocidal polymers are well-known in the art and becoming increasingly important in order to contain and control the spread of infectious pathogens in a variety of health and industrial applications. To this end, biocidal polymers have been developed for use in solution form as well as to incorporate biocidal activity onto materials via coatings.

Therefore, it would be highly desirable to have a solution of a biocidal polymer having both biocidal and biocompatibility properties for a prolonged storage period. It is, therefore, desirable to have a ready-to-use biocidal product which prevents fast reticulation in volume, thereby prolonging storage period.

BRIEF SUMMARY OF THE INVENTION

To address shortcomings of prior art, the inventors studied and meticulously determined the reaction period during which polyvinylpyridine (PVP), monomer A and monomer B are reacted in an alcoholic solution to prepare a statistical copolymer having both biocidal and biocompatible properties.

The present invention, therefore, provides a ready-to-use alcoholic solution of biocidal copolymer designed to be stable for a prolonged storage period with no spontaneous volume reticulation. According to the present invention, the alcoholic solution comprises a biocidally active partially quaternarized polyvinylpyridine polymer.

In another aspect, the present invention also provides a one-step process to prepare a ready-to-use alcoholic solution of biocidal copolymer, which is stable and prevents reticulation in volume during the storage period. According to the present invention, the process comprises a step of reacting polyvinylpyridine (PVP), monomer A and monomer B in an alcoholic solution for a desired reaction period to obtain a biocidally active partially quaternarized polyvinylpyridine polymer.

The present invention further provides a one-step process to prepare a statistical copolymer by reacting polyvinylpyridine, monomer A and monomer B in an alcoholic solution. According to the present invention, monomer A is used in 5% fixed proportion to achieve stability of the solution and prevent reticulation in volume during the storage period.

BRIEF DESCRIPTION OF THE DRAWINGS

The following detailed description of preferred embodiments of the invention, will be better understood when read in conjunction with the appended drawings. For the purpose of illustration, there is shown in the drawings an embodiment which is presently preferred. It should be understood, however, that the invention is not limited to the precise arrangements and instrumentalities shown.

Figure 2:
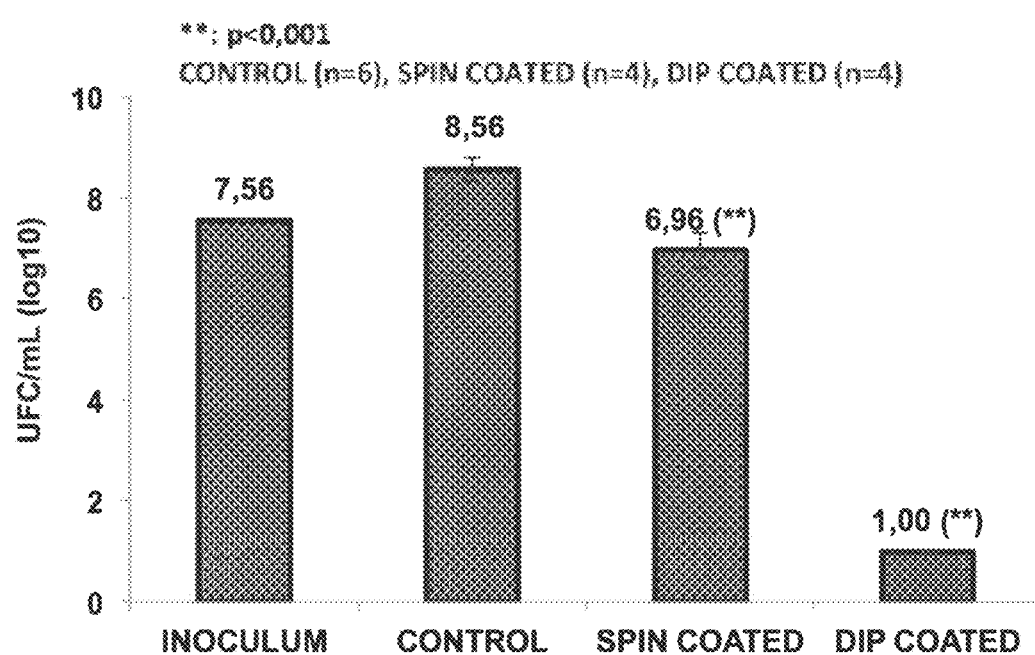
Figure 3:
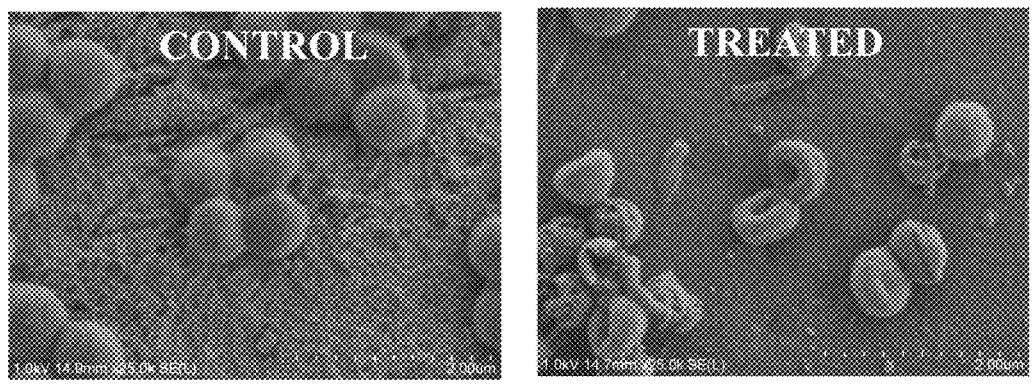
Figure 4:
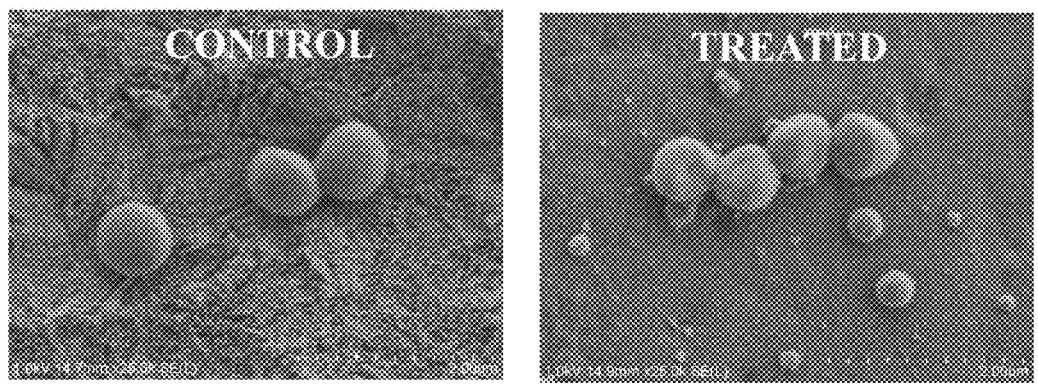
Figure 5:
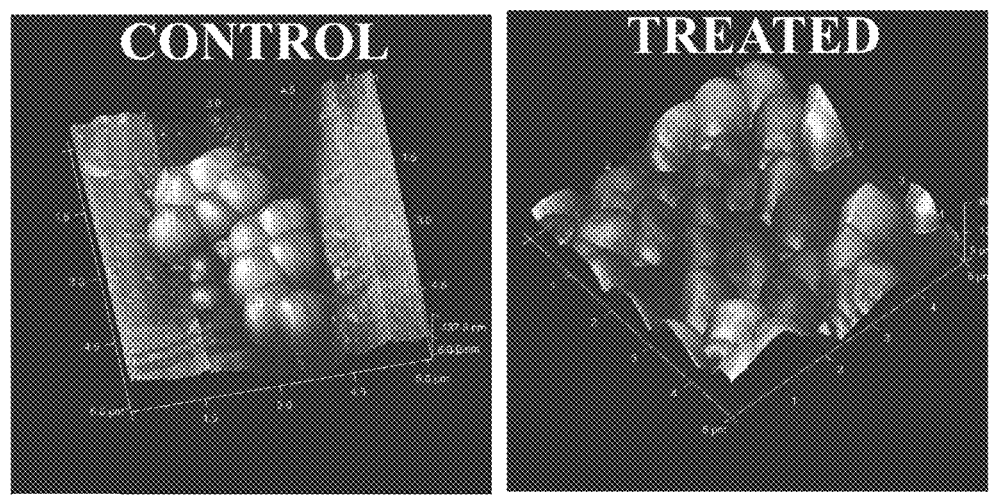
Figure 6:
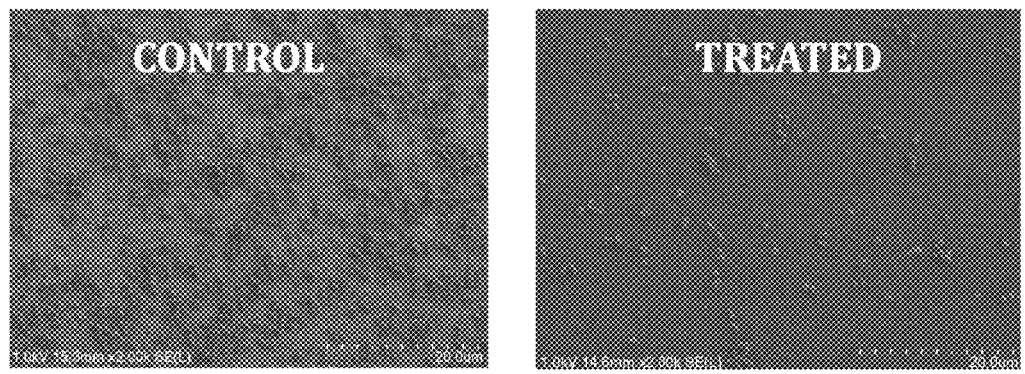
Figure 7:
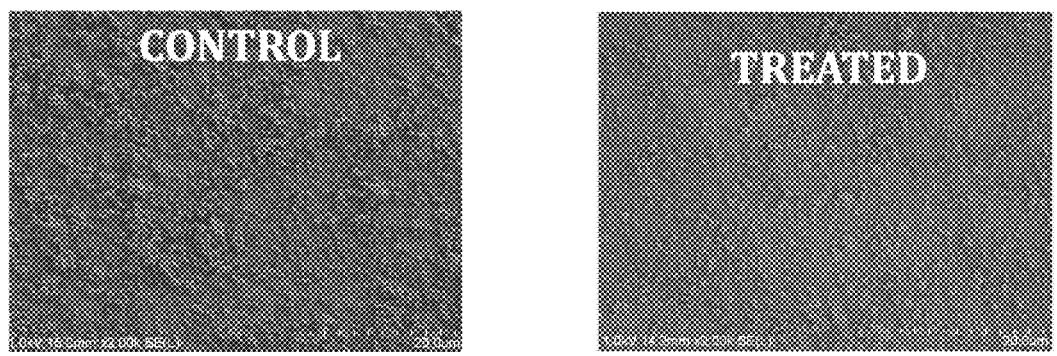
Figure 8:
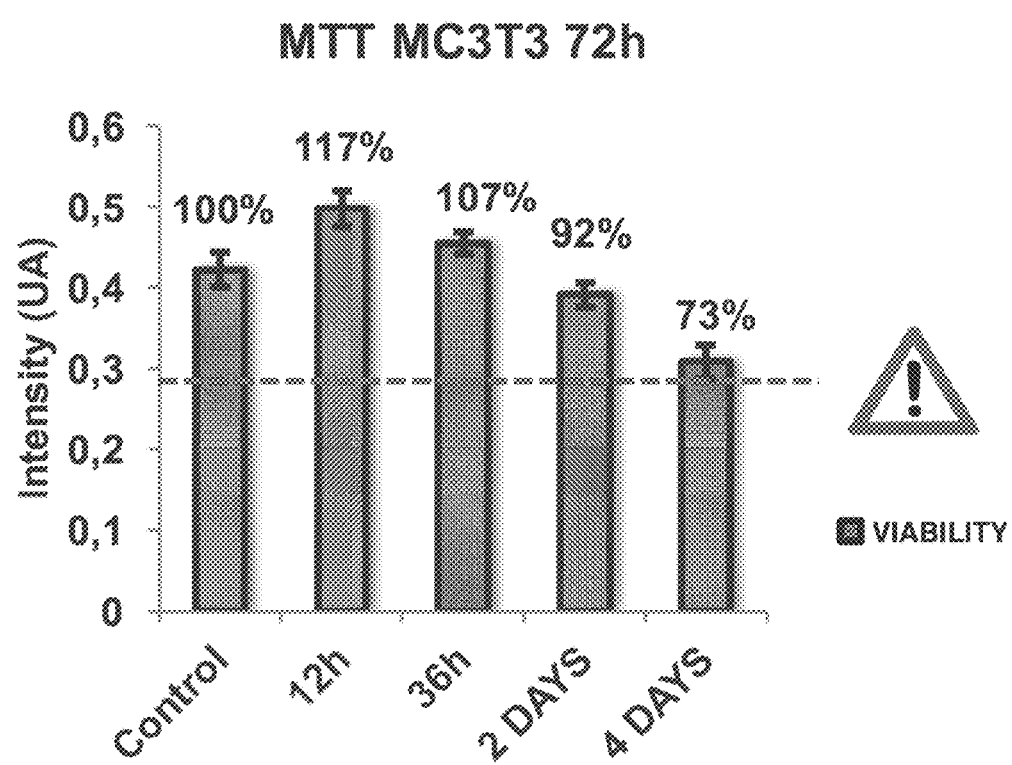
Figure 9:
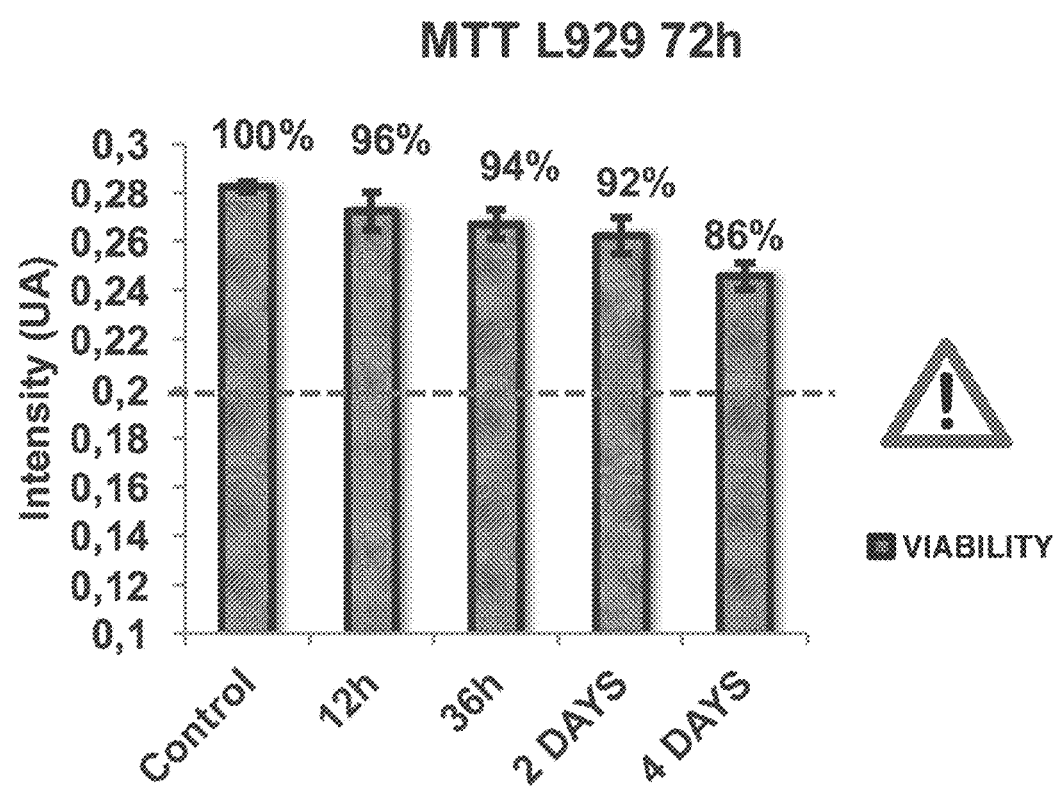
Figure 10:
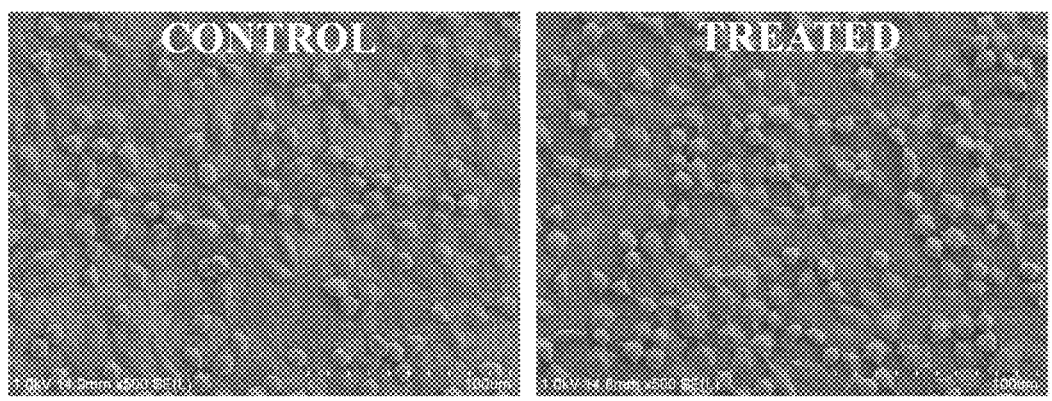

ratio using the area ratio between the stretching mode of the C—$N^+$ band (1640 $cm^{-1}$) and C—N band (1600 $cm^{-1}$);

FIG. 2 represents MRSA (Methicillin-resistant *Staphylococcus aureus*) bacterial killing at 37° C. in rich medium (Brain-Heart Infusion, BHI) after 1 hour with a $10^7$ CFU/mL inoculum (CFU: Colony Forming Units);

FIG. 3 represents MRSA (Methicillin-resistant *Staphylococcus aureus*) in vitro biofilm (Brain-Heart Infusion, BHI) after 3 days on titanium plates (spin-coated treated surface vs. control) at 37° C. using scanning-electron microscopy with field-emission gun with a $10^7$ CFU/mL inoculum (CFU: Colony Forming Units);

FIG. 4 represents MRSA (Methicillin-resistant *Staphylococcus aureus*) in vitro biofilm (Brain-Heart Infusion, BHI) after 24 hours on titanium plates (spin-coated treated surface vs. control) at 37° C. using scanning-electron microscopy with field-emission gun with a $10^7$ CFU/mL inoculum (CFU: Colony Forming Units);

FIG. 5 represents a young MRSA (Methicillin-resistant *Staphylococcus aureus*) biofilm (Brain-Heart Infusion, BHI) after 3 hours on titanium surfaces (spin-coated treated vs. control) at 37° C. using Atomic Force Microscopy (AFM) with a $10^7$ CFU/mL inoculum (CFU: Colony Forming Units);

FIG. 6 represents a young MRSA (Methicillin-resistant *Staphylococcus aureus*) biofilm (Brain-Heart Infusion, BHI) after 6 hours on titanium plates (spin coated treated vs. controls) at 37° C. using scanning-electron microscopy with field-emission gun with a $10^7$ CFU/mL inoculum (CFU: Colony Forming Units);

FIG. 7 represents a mature MRSA (Methicillin-resistant *Staphylococcus aureus*) biofilm (Brain-Heart Infusion, BHI) after 7 days on titanium plates (spin coated treated vs controls) at 37° C. using scanning-electron microscopy with field-emission gun with a $10^7$ CFU/mL inoculum (CFU: Colony Forming Units);

FIG. 8 represents MC3T3 (murine osteoblast precursor cell line) cell viability (MTT-assay) after a 72-hour contact on control and grafted titanium of varying surface cationic densities;

FIG. 9 represents L929 (murine fibroblast cell line) cell viability (MTT-assay) after a 72-hour contact on control and grafted titanium of varying surface cationic densities; and FIG. 10 represents L929 (murine fibroblast cell line) cell aspect after a 72 h culture on titanium plates (spin-coated or controls) using scanning-electron microscopy with field-emission gun.

DETAILED DESCRIPTION OF THE INVENTION

Certain terminology is used in the following description for convenience only and is not limiting. The words "right", "left", "lower", and "upper" designate directions in the drawings to which reference is made. The terminology includes the above-listed words, derivatives thereof, and words of similar import. Additionally, the words "a" and "an" mean "at least one." Further, the skilled artisan will understand that the present invention can be practiced without employing the specific details provided herein, or that it can be used for purposes other than those described herein. The drawings and descriptions are intended to be exemplary of various aspects of the present invention and are not intended to narrow the scope of the appended claims.

Unless defined otherwise, all technical and scientific terms used herein have the same meaning as commonly understood by one of ordinary skill in the art to which this invention belongs.

The term "biocide", as used herein, means a chemical compound, a chemical composition, a chemical formulation which can kill or render harmless a microorganism exemplified by bacterium, yeast, and fungi.

The term "copolymer" as used herein is defined as a polymer that is made up of more than one type of monomer.

The terms "halo" or "halogen" by themselves or as part of another substituent, have the same meaning as commonly understood by one of ordinary skill in the art, and preferably refer to chlorine, bromine or iodine atom.

The expression "statistical copolymer" as used herein is defined as a copolymer that is made up of more than one monomer, and in which the different monomer units are randomly distributed in the polymeric chain. Unless stated otherwise, the terms "copolymer", "biocidal polymer", and "partially quaternarized polyvinyl pyridine" refer to statistical copolymer.

The present invention provides a ready-to-use alcoholic solution of a partially quaternarized polyvinylpyridine polymer having both biocidal and biocompatibility properties, which is stable and prevents reticulation in volume during the storage period.

In particular, the present invention provides an alcoholic solution of a biocidally active polymer and methods of preparing the same. The solution comprises a biocidally active partially quaternarized polyvinylpyridine polymer obtained by reacting polyvinylpyridine (PVP) with combinations of monomer A and monomer B in an alcoholic solution. It was surprisingly discovered that polyvinylpyridine (PVP), when reacted with combinations of monomer A and monomer B in an alcoholic solution for a reaction period of two days, resulted in a statistical copolymer that showed biocidal and biocompatibility properties simultaneously. The solution was found stable and prevented reticulation in volume during the storage period when monomer A was used in 5% fixed proportion, thus prolonging the storage period.

It was further surprisingly discovered that quaternarization of a pyridine nucleus with monomer A was kinetically faster than with the monomer B in alcoholic solution. The quaternarization with the monomer B led to a

ratio, which was found to be dependent on the reaction period. The inventors studied and found a specific

ratio and reaction period which resulted in a statistical copolymer that showed both biocidal and biocompatibility properties simultaneously.

According to the embodiments of the invention, the specific

ratio is 44±2% and the reaction period is two days for obtaining a statistical copolymer having biocidal and biocompatibility properties simultaneously.

Statistical Copolymer

The statistical copolymer according to the present invention according to scheme 1 or scheme 2 contains a monomer A to immobilize the polymeric chain on the activated surface through a covalent bond between the surface and the polymeric moiety and a monomer B to obtain a specific

ratio and improve biocompatibility.

The monomer A is selected for its ability to anchor to the activated surface. According to preferred embodiments of the invention, the monomer A that may be part of the statistical copolymer preferably includes iodopropyltrimethyoxysilane (used in scheme 1) or chloromethylcatechol (used in scheme 2). The monomer A is preferably used in 5% fixed proportion to achieve stability of the solution and prevent reticulation in volume during the storage period.

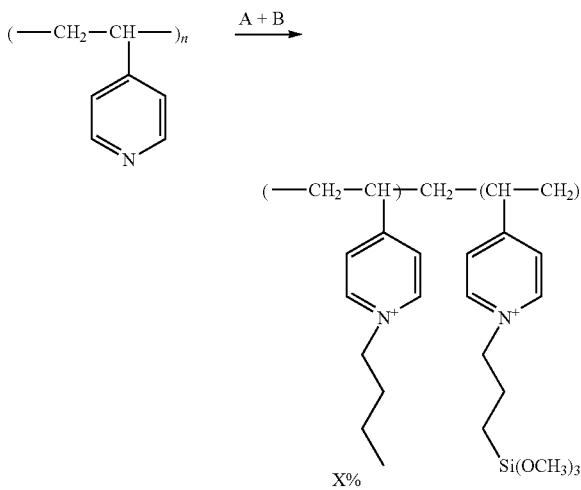

SCHEME 1 n: 1 Eq
A: 20 to 50 mEq
B: 1 Eq
x depends on reaction time

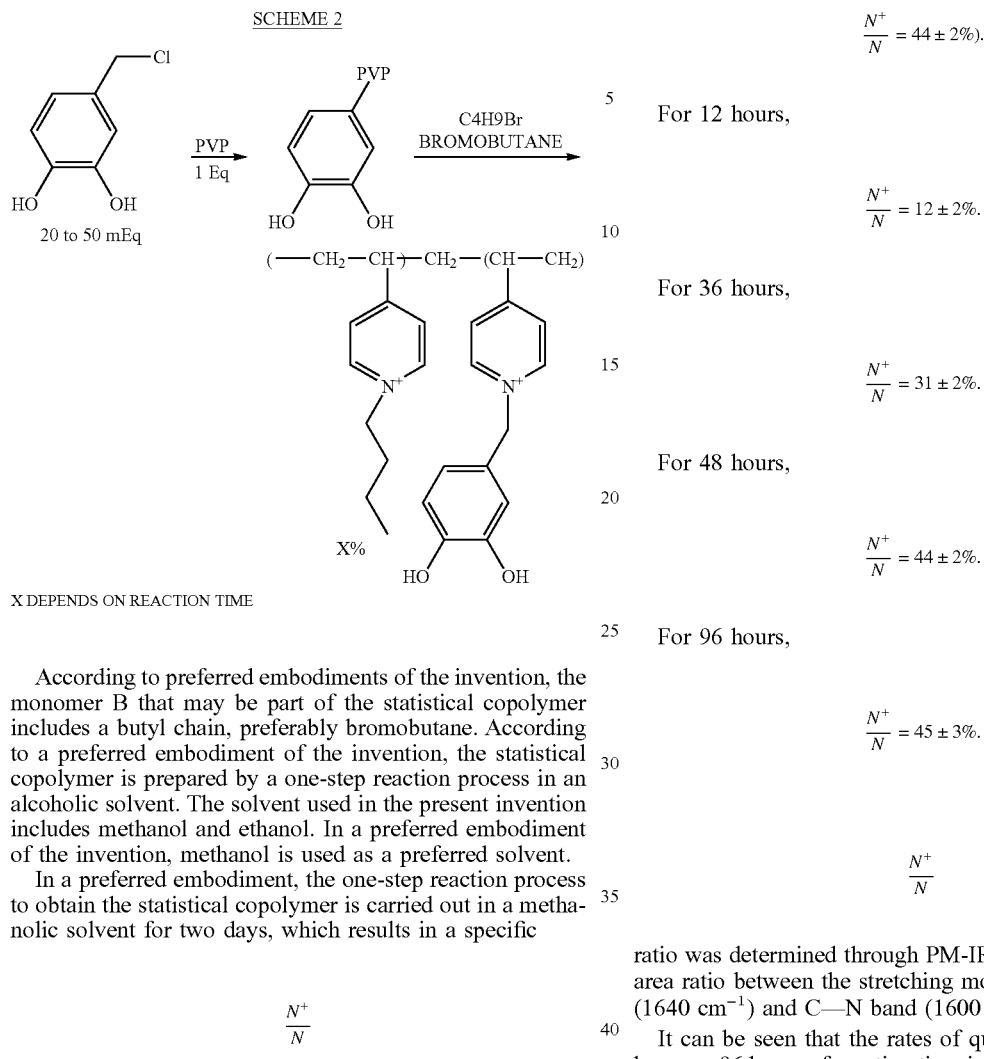

SCHEME 2

X DEPENDS ON REACTION TIME

According to preferred embodiments of the invention, the monomer B that may be part of the statistical copolymer includes a butyl chain, preferably bromobutane. According to a preferred embodiment of the invention, the statistical copolymer is prepared by a one-step reaction process in an alcoholic solvent. The solvent used in the present invention includes methanol and ethanol. In a preferred embodiment of the invention, methanol is used as a preferred solvent.

In a preferred embodiment, the one-step reaction process to obtain the statistical copolymer is carried out in a methanolic solvent for two days, which results in a specific $$\frac{N^+}{N}$$

ratio of 44±2%.

The biocidal polymer of the present invention can be used on various surfaces including titanium and titanium alloys, iron, ceramics, steel, polyethylene (low and high reticulation for use in biomedical implants, after prior plasma activation), teflon (after prior plasma activation), polyethylene terephthalate (after prior plasma activation), and polypropylene (low and high density, after prior plasma activation), cotton, silicon, wood, glass, and all cellulosic compounds. It will be understood that this is a non-exhaustive list. The biocidal polymer of the present invention can be used to contain and control the spread of infectious pathogens in a variety of health and industrial applications.

The following examples are included solely to provide a clearer and more consistent understanding of the present invention.

Figure 1:
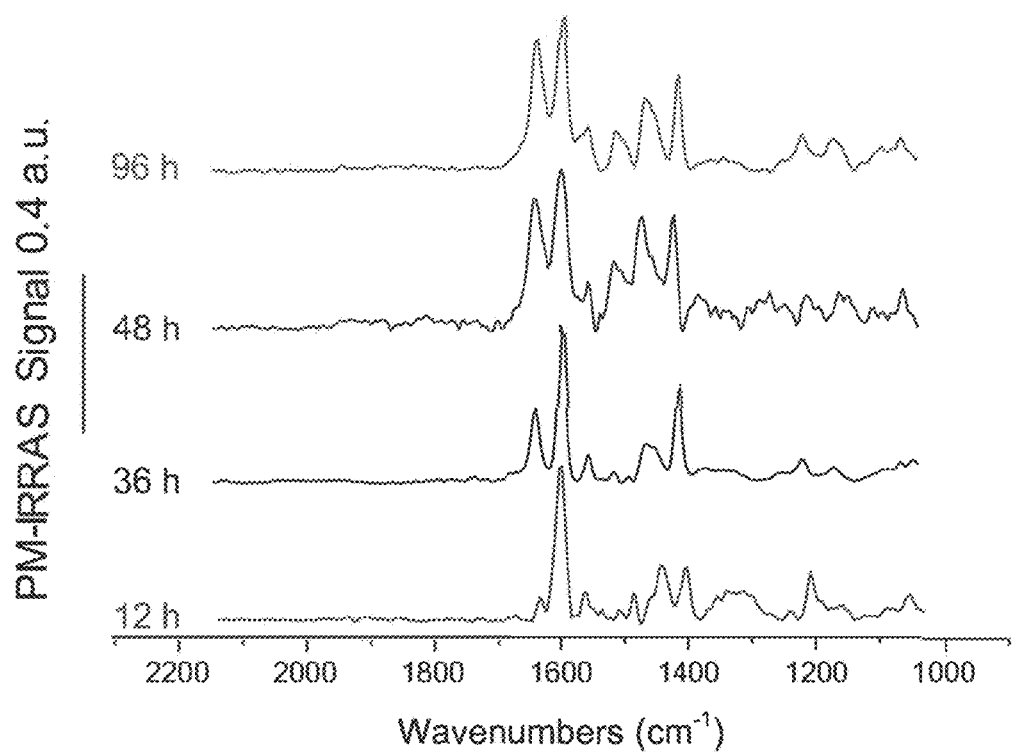
FIG. 1 represents PM-IRRAS spectra to determine the $$\frac{N^+}{N}$$

Example 1 (FIG. 1)

Synthesis of a Statistical Copolymer Using Iodopropyltrimethoxysilane

Polyvinylpyridine (PVP) was reacted with iodopropyltrimethoxysilane (50 mEq) and bromobutane (1 Eq) in boiling methanol in a one-step process for a reaction time of two days to obtain biocidal and biocompatibility simultaneously (48 hours, $$\frac{N^+}{N} = 44 \pm 2\%).$$

For 12 hours, $$\frac{N^+}{N} = 12 \pm 2\%.$$

For 36 hours, $$\frac{N^+}{N} = 31 \pm 2\%.$$

For 48 hours, $$\frac{N^+}{N} = 44 \pm 2\%.$$

For 96 hours, $$\frac{N^+}{N} = 45 \pm 3\%.$$

$$\frac{N^+}{N}$$

ratio was determined through PM-IRRAS spectra using the area ratio between the stretching mode of the C—N$^+$ band (1640 cm$^{-1}$) and C—N band (1600 cm$^{-1}$).

It can be seen that the rates of quaternarization after 48 hours or 96 hours of reaction time in refluxing methanol are the same within the accuracy of measurement. Using PM-IRRAS spectra following deposition and copolymer grafting on titanium, it was observed that quaternarization increased with reaction time (12 h to 96 h) (FIG. 1).

Example 2

Grafting of Titanium Surface

The solution of statistical copolymer as prepared using scheme of Example 1 was distributed and covalently grafted on a polished (4000 grit paper) and activated titanium (piranha solution or plasma activation) surface using an iodopropyltrimethoxysilane chain.

Example 3

Synthesis of a Statistical Copolymer Using Chloromethylcatechol

Polyvinylpyridine (PVP) was reacted with chloromethylcatechol (20 to 50 mEq) and bromobutane (1 Eq) in boiling methanol in a one-step process for a reaction time of two days to obtain biocidal and biocompatibility properties simultaneously.

For 48 hours, $$\frac{N^+}{N} = 44 \pm 2\%.$$

$$\frac{N^+}{N}$$

ratio was determined through PM-IRRAS spectra using the area ratio between the stretching mode of the C—$N^+$ band (1640 $cm^{-1}$) and C—N band (1600 $cm^{-1}$).

Example 4

Grafting of a Titanium Surface

The solution of statistical copolymer as prepared by Example 3 was distributed and covalently grafted on the activated titanium surface using a chloromethylcatechol chain.

Example 5 (FIG. 2)

Deposition of the Copolymer on a Titanium Surface

Grafted titanium surfaces showed a high bactericidal effect in vitro against methicillinresistant *Staphyloccocus aureus* (MRSA) within 1 hour under proliferating conditions (37° C., B.H.I, Brain Heart Infusion medium). The effect depended on the thickness of the grafted layer. Spin coated (8 nm monolayer) surfaces showed an average 99% bactericidal activity in vitro within 1 hour. Thicker coatings achieved 100% sterilization of surfaces within 1 hour. Inhibition growth activity against MRSA showed a 1.6 $log_{10}$ inhibition with spin coated surfaces and still 100% sterilization with thicker coatings. The bars in FIG. 2. display control and treated plates bacterial counts following 1-hour contact with a 20 μL bacterial suspension (107 CFU/ml inoculum) applied on the surface with a cover-slip.

Example 6 (FIG. 3, FIG. 4, FIG. 5, FIG. 6, FIG. 7)

Deposition of the Copolymer on Titanium

Grafted titanium surfaces showed a high in vitro antibiofilm activity against MRSA under proliferating conditions (37° C., Brain Heart Infusion, Medium Change every 24 hours, $10^7$ CFU/mL inoculum) up to 7 days. Scanning Electron Microscopy with Field Emission Gun (SEM-FEG) findings showed a membrane perforation of bacteria, bacterial shrinkage, reduction of adherent bacteria and biofilm thickness. FIGS. 3-4 show bacterial perforation and shrinkage on the coated titanium. FIG. 5 shows bacterial perforation and volume shrinkage on the treated surfaces. FIG. 6 shows low bacterial surface density on the treated titanium. FIG. 7 shows low bacterial surface density on the treated titanium and multi-layer bacterial aspect on the control titanium. Atomic force microscopy findings confirmed these morphologic modifications.

Example 7 (FIG. 8, FIG. 9, FIG. 10)

Determination of Biocompatibility Property

L929 (murine fibroblast cell line) cells were cultured in DMEM (Dulbecco's Mod Eagle Medium) supplemented with 10% FBS (fetal bovine serum), 2 mM glutamin, 100 mug/mL streptomycin and 100 mug/mL penicillin. MC3T3 (murine osteoblast precursor cell line) cells were cultured in MEM-α (Gibco Invitrogen, France) enriched with 10% FBS (fetal bovine serum), 2 mM glutamin, 100 U/mL penicillin, and 100 μg/mL streptomycin. After incubation at 37° C. in humid atmosphere and 5% $CO_2$, a trypsin EDTA (ethylenediaminetetraacetic acid) treatment was applied in order to retrieve all the adherent cells. $5 \times 10^5$ cells of each line were seeded on each titanium plate in a volume of 1 mL of their respective culture medium within 24-well cell culture plates. Then, an MTT-assay (3-(4,5-dimethylthiazol-2-yl)-2,5-diphenyltetrazolium bromide) was performed by comparing the optical densities of the studied media at 550 nm in order to deduce cell survival at 72 hours. Interestingly, copolymers synthesized according to the same process in only 12 hours with no lateral butyl chain did not show biocidal activity, but significantly enhanced osteoblast adhesion and survival at 72 hours. Such coatings might be of interest to facilitate implant osteointegration.

Referring to FIG. 8, MC3T3 cell viability decreased with higher surface cationic densities (past 12 hour reaction time). Cationic densities were related with reaction time. Optical density was 550 nm. If the reaction time was 12 hours, cells deposited on grafted titanium surfaces persistently showed higher cell survival at 72 hour than cells on control titanium plates. If the reaction lasted 4 days, survival decreased to the critical level of viability.

Referring to FIG. 9, L929 (murine fibroblast cell line) cell viability decreased with higher reaction time or surface cationic densities. Surface cationic densities were related with reaction time. L929 cells showed better tolerance of higher surface cationic densities compared with MC3T3 cells. Optical density was 550 nm.

Referring to FIG. 10, a similar morphological aspect and density was observed.

SEM-FEG (Scanning-electron microscopy with field emission gun) images were obtained using polished control titanium plates or titanium plates grafted with the described copolymer synthesized in 2 days of reaction time. Cells had similar morphologic patterns on control and grafted plates.

In conclusion, biocompatibility assessments (MTT-assay to determine cell metabolic activity) showed a good to excellent cell viability on two cell lines (fibroblasts L929 and preosteoblasts MC3T3) after 72 hours in vitro, depending on surface cationic density. A higher cationic density resulted in a decreased survival at 72 hours.

Example 8

A potential application against wood-boring insects is grafting the copolymer with a maximum reaction yield on wood cellulose. The mechanism would be direct or indirect. The direct mechanism comprises grafting a biocidal copolymer on cellulose in order to prevent cellulose digestion by cellulose-eating insects' digestive enzymes (such as Cx-cellulase or others). The indirect mechanism consists of killing the protozoa, bacteria or fungi that are responsible for the production of such enzymes (such as C1-cellulase or others) in cellulose-eating insects' gastrointestinal system.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. An alcoholic solution comprising a polyvinylpyridine polymer of formula I or formula II:

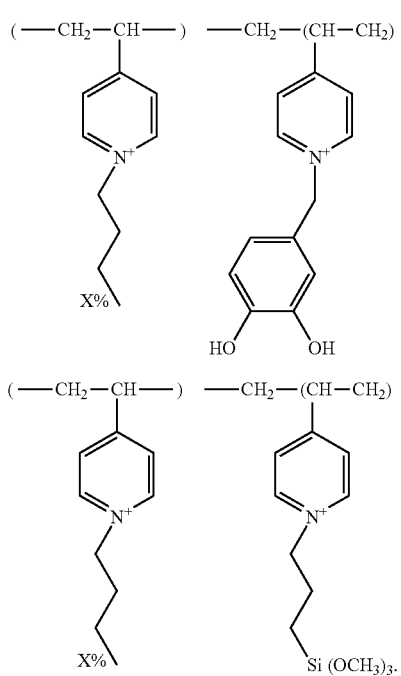

wherein X is 12±2% to 45±2%.

2. The alcoholic solution of claim 1, wherein the polymer of formula I is a copolymer of obtained by reacting polyvinylpyridine, chloromethylcatechol and bromobutane.

3. The alcoholic solution of claim 2,
wherein the copolymer is prepared by a one-step process reaction in an alcoholic solvent,
wherein the alcoholic solvent is one of methanol and ethanol, and
wherein the one-step process reaction is carried out for two days.

4. The alcoholic solution of claim 1, wherein the polymer of formula II is a copolymer obtained by reacting polyvinylpyridine, iodopropyltrimethoxysilane and bromobutane.

5. The alcoholic solution of claim 4,
wherein the copolymer is prepared by a one-step process reaction in an alcoholic solvent,
wherein the alcoholic solvent is one of methanol and ethanol, and
wherein the one-step process reaction is carried out for two days.

6. The alcoholic solution of claim 1, wherein X is 44±2%.

7. The alcoholic solution of claim 6, wherein the polyvinylpyridine polymer of formula I or formula II is biocompatible.

8. The alcoholic solution of claim 3, wherein X is 44±2%.

9. The alcoholic solution of claim 8, wherein the polyvinylpyridine polymer of formula I biocompatible.

10. The alcoholic solution of claim 5, wherein X is 44±2%.

11. The alcoholic solution of claim 10, wherein the polyvinylpyridine polymer of formula I biocompatible.

* * * * *